(12) United States Patent
Hsieh et al.

(10) Patent No.: US 9,778,191 B2
(45) Date of Patent: Oct. 3, 2017

(54) OPTICAL SENSING MODULE

(71) Applicant: Personal Genomics, Inc., Grand Cayman OT (KY)

(72) Inventors: Hsin-Yi Hsieh, Taoyuan (TW); Sheng-Fu Lin, New Taipei (TW); Teng-Chien Yu, Hsinchu (TW)

(73) Assignee: Personal Genomics, Inc., Grand Cayman (KY)

( * ) Notice: Subject to any disclaimer, the term of this patent is extended or adjusted under 35 U.S.C. 154(b) by 0 days.

(21) Appl. No.: 15/422,474

(22) Filed: Feb. 2, 2017

(65) Prior Publication Data
US 2017/0227465 A1 Aug. 10, 2017

Related U.S. Application Data

(60) Provisional application No. 62/291,532, filed on Feb. 5, 2016.

(51) Int. Cl.
*G01N 21/64* (2006.01)
*G02B 6/00* (2006.01)
*F21V 8/00* (2006.01)

(52) U.S. Cl.
CPC ......... *G01N 21/6454* (2013.01); *G02B 6/005* (2013.01); *G02B 6/0036* (2013.01); *G01N 2021/6471* (2013.01); *G01N 2021/6478* (2013.01); *G01N 2201/0642* (2013.01)

(58) Field of Classification Search
CPC ....... G01N 21/6454; G01N 2021/6471; G01N 2021/6478; G01N 2201/0642; G02B 6/0036; G02B 6/005
See application file for complete search history.

(56) References Cited

U.S. PATENT DOCUMENTS

| | | | |
|---|---|---|---|
| 9,624,540 B2* | 4/2017 | Lundquist | C12Q 1/6874 |
| 2010/0065726 A1* | 3/2010 | Zhong | G01N 21/648 250/227.24 |
| 2010/0278480 A1* | 11/2010 | Vasylyev | G02B 3/005 385/33 |
| 2011/0117637 A1* | 5/2011 | Gray | G01N 21/6452 435/287.2 |
| 2013/0043500 A1* | 2/2013 | Orita | G02F 1/133602 257/98 |
| 2014/0168572 A1* | 6/2014 | Iwata | H01L 51/5268 349/61 |
| 2014/0199016 A1* | 7/2014 | Grot | G02B 6/10 385/11 |

(Continued)

*Primary Examiner* — Mark R Gaworecki
(74) *Attorney, Agent, or Firm* — Jianq Chyun IP Office

(57) ABSTRACT

An optical sensing module is configured to detect a characteristic of a sample. The optical sensing module includes a light source, a light guide plate, a first cladding layer, a light converging layer, a filter layer, and a plurality of sensors. The light source is configured to provide an exciting beam. Positions of the sensors correspond to positions of the holes. After the exciting beam enters the light guide plate, at least one portion of the exciting beam is transmitted to the sample through a portion of the surface of the light guide plate exposed by the holes, the sample is excited by the exciting beam to emit a signal beam, and the signal beam passes through the light converging layer and the filter layer in an order and travels to the sensors. Another optical sensing module is also provided.

17 Claims, 11 Drawing Sheets

(56) References Cited

U.S. PATENT DOCUMENTS

2014/0287964 A1* 9/2014 Lundquist ............ C12Q 1/6874
 506/38
2014/0367589 A1* 12/2014 Chiou .................... B82Y 15/00
 250/458.1

* cited by examiner

OPTICAL SENSING MODULE

CROSS REFERENCE TO RELATED APPLICATION

This application claims the priority benefit of U.S. provisional application Ser. No. 62/291,532, filed on Feb. 5, 2016. The entirety of the above-mentioned patent application is hereby incorporated by reference herein and made a part of specification.

BACKGROUND OF THE INVENTION

1. Field of the Invention

The invention generally relates to a sensing module, in particular, to an optical sensing module.

2. Description of Related Art

In a conventional fluorescence detection system, a sample is excited by an exciting beam to emit a fluorescent light. The fluorescent light from the sample is transmitted to a light sensor, and the light sensor converts the fluorescent light into electrical signals. A processor in the fluorescence detection system analyzes the electrical signals to learn the information of the sample.

Under normal circumstances, a filter layer is additionally disposed in the fluorescence detection system in order to filter a portion of the exciting beam for preventing the exciting beam from affecting the sensing results. Nevertheless, the filter layer also filters a portion of the fluorescence and affects sensitivity of the sensing results.

SUMMARY OF THE INVENTION

The invention provides an optical sensing module with a high signal-noise ratio (SNR) and high sensitivity.

An embodiment of the invention provides an optical sensing module. The optical sensing module is configured to detect a characteristic of a sample. The optical sensing module includes a light source, a light guide plate, a first cladding layer, a light converging layer, a filter layer, and a plurality of sensors. The light source is configured to provide an exciting beam. The light guide plate has a first side and a second side opposite to each other. The first cladding layer is disposed at the first side of the light guide plate. The first cladding layer has a plurality of holes. The holes expose a portion of a surface of the light guide plate. The sample is placed in at least one of the holes. The light converging layer is disposed at the second side of the light guide plate. Positions of the sensors correspond to positions of the holes. After the exciting beam enters the light guide plate, at least one portion of the exciting beam is transmitted to the sample through the portion of the surface of the light guide plate exposed by the holes, the sample is excited by the exciting beam to emit a signal beam, and the signal beam passes through the light converging layer and the filter layer in an order and travels to the sensors.

In an embodiment of the invention, the light converging layer includes a plurality of light converging lenses, and positions of the light converging lenses correspond to the positions of the holes.

In an embodiment of the invention, the light converging layer includes a substrate and a covering layer. The covering layer includes a base and a plurality of light converging structures. The light converging structures are arranged on the base and face the filter layer, and the covering layer covers the substrate.

In an embodiment of the invention, the light converging structures includes a plurality of triangular columnar structures. The triangular columnar structures extend in a first direction, and the exciting beam propagates along a second direction. The first direction is perpendicular to the second direction.

In an embodiment of the invention, the light converging structures include a plurality of trigonal tapers, a plurality of cones, or a plurality of trapezoidal pillar structures.

In an embodiment of the invention, the light converging layer includes a plurality of first light functional elements and a plurality of second light functional elements. Positions of the first light functional elements correspond to positions of the holes. Any one of the first light functional elements is located between two adjacent second light functional elements.

In an embodiment of the invention, the first light functional elements include a plurality of first light converging elements, and the second light functional elements include a plurality of second light converging elements.

In an embodiment of the invention, the first light functional elements include a plurality of light transmitting elements, and the second light functional elements include a plurality of light shielding elements.

In an embodiment of the invention, the first light functional elements include a plurality of first light converging elements, and the second light functional elements include a plurality of light shielding elements.

In an embodiment of the invention, the first light functional elements include a plurality of first light transmitting elements, and the second light functional elements include a plurality of light absorbing elements and a plurality of second light transmitting elements.

In an embodiment of the invention, the first light functional elements include a plurality of light transmitting elements, and the second light functional elements include a plurality of second light converging elements.

In an embodiment of the invention, the light converging layer is disposed between the light guide plate and the filter layer.

In an embodiment of the invention, the light converging layer is disposed between the filter layer and the sensors.

In an embodiment of the invention, the optical sensing module further includes a passivation layer disposed between the filter layer and the sensors.

In an embodiment of the invention, the optical sensing module further includes a second cladding layer disposed between the light guide plate and the light converging layer.

In an embodiment of the invention, the filter layer includes an absorption filter layer or an interference filter layer.

An embodiment of the invention provides an optical sensing module. The optical sensing module is configured to detect a characteristic of a sample. The optical sensing module includes a light source, a light guide plate, a first cladding layer, a noise-reduction layer, and a plurality of sensors. The light source is configured to provide an exciting beam. The light guide plate has a first side and a second side opposite to each other. The first cladding layer is disposed at the first side of the light guide plate. The first cladding layer has a plurality of holes. The holes expose a portion of a surface of the light guide plate. The sample is placed in at least one of the holes. The noise-reduction layer includes a plurality of filter elements and a plurality of light shielding elements. Positions of the filter elements correspond to positions of the holes. Any one of the light shielding elements is located between two adjacent filter elements.

Positions of the sensors correspond to positions of the holes. After the exciting beam enters the light guide plate, at least one portion of the exciting beam is transmitted to the sample through the portion of the surface of the light guide plate exposed by the holes. The sample is excited by the exciting beam to emit a signal beam, and a first portion of the signal beam passes through at least one of the filter elements and travels to the sensor. A second portion of the signal beam is shielded by at least one of the light shielding elements.

In view of the forgoing, in the optical sensing module provided in the embodiments of the invention, the signal beam passes through the light converging layer in an order and travels to the sensors. The light converging layer provides a converging function, and the filter layer provides a filtering function. Hence, the optical sensing module provided in the embodiments of the invention has high sensitivity and high SNR.

On the other hand, in the optical sensing module provided in the embodiments of the invention, the first portion of the signal beam is filtered by the filter elements, and the second portion of the signal beam is shielded by the light shielding elements. The optical sensing module can achieve a filtering function and a light converging function by the noise-reduction layer and has a small thickness. Furthermore, crosstalk phenomenon between any two adjacent sensors can be prevented due to the noise-reduction later. Therefore, the optical sensing module provided in the embodiments of the invention has high sensitivity, high SNR, and small thickness.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
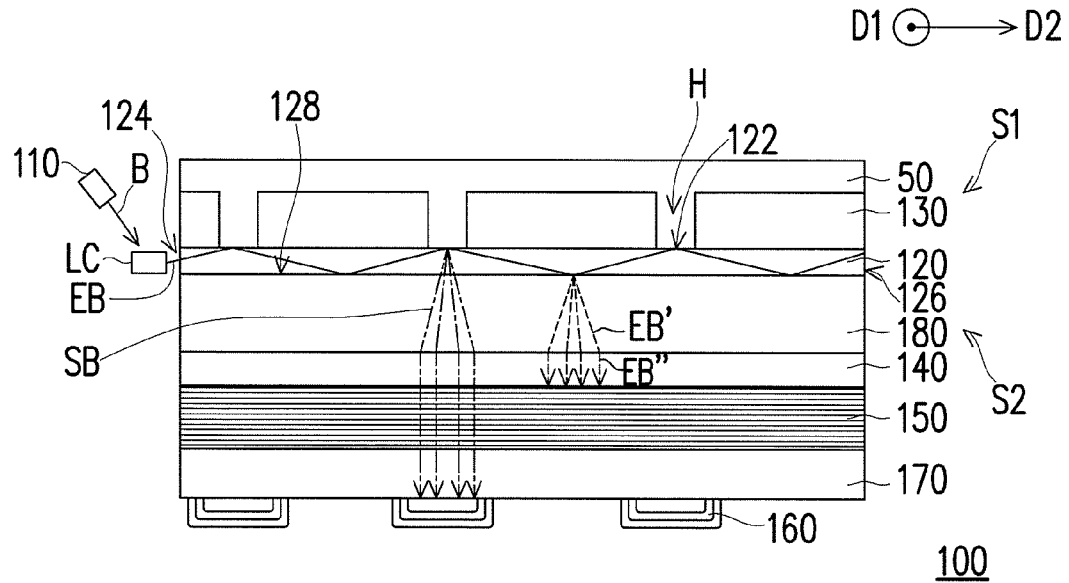
FIG. 1 is a schematic cross-sectional view of an optical sensing module according to an embodiment of the invention.

Reference will now be made in detail to the embodiments of the invention, examples of which are illustrated in the accompanying drawings. Wherever possible, the same reference numbers are used in the drawings and the description to refer to the same or like parts.

FIG. 1 is a schematic cross-sectional view of an optical sensing module according to an embodiment of the invention.

Referring to the FIG. 1, in the embodiment of the invention, the optical sensing module 100 is configured to detect a characteristic of a sample 50. The sample 50 is, for example, a fluorescent material, but the invention is not limited thereto. The optical sensing module 100 includes a light source 110, a light guide plate 120, a first cladding layer 130, a light converging layer 140, a filter layer 150, and a plurality of sensors 160. The light guide plate 120 has a first side S1 and a second side S2 opposite to each other. The light source 110 is configured to provide an exciting beam EB. The first cladding layer 130 is disposed at the first side S1 of the light guide plate 120. The first cladding layer 130 has a plurality of holes H. The holes H are, for example, sample wells, but the invention is not limited thereto. The sample 50 is placed in at least one of the holes H. To be more specific, in the embodiment, the sample 50 is placed in the holes H. The bottoms of the holes H are adjacent to the light guide plate 120. The holes H expose a portion of the surface 122 of the light guide plate 120. The light converging layer 140 is disposed at the second side S2 of the light guide plate 120. Positions of the sensors 160 correspond to positions of the holes H. The light converging layer 140 is disposed between the light guide plate 120 and the filter layer 150. The filter layer 150 is, for example, an interference filter layer formed by a plurality of optical films. In other embodiments, the filter layer 150 can be an absorption filter layer, but the invention is not limited thereto. In the embodiment, each of the sensors 160 is, for example, a photodiode with a plurality of junctions. The photodiode is configured to receive light beams and correspondingly generate electrical signals.

Referring to FIG. 1 again, in the embodiment, the optical sensing module 100 further includes a passivation layer 170 and a second cladding layer 180. The passivation layer 170 is disposed between the filter layer 150 and the sensors 160.

The second cladding layer 180 is disposed between the light guide plate 120 and the light converging layer 140. A material of the second cladding layer 180 is, for example, silicon dioxide or air, but the invention is not limited thereto. In detail, the light guide plate 120 is sandwiched between the first cladding layer 130 and the second cladding layer 180. The refractive indexes of the first cladding layer 130 and the second cladding layer 180 are smaller than a refractive index of the light guide plate 120. The passivation layer 170 also provides a cladding function and an insulation function to ensure stability of the sensors 160.

In the embodiment, the light source 110 is, for example, disposed beside the light guide plate 120. In the embodiment, the optical sensing module 100 further includes a light coupler LC. The light source 110 provides a light beam B, which may be at least partially coupled into the light guide plate 120 by the light coupler LC. The light beam B coupled into the light guide plate 120 through the light entrance surface 124 serves as the exciting beam EB. The exciting beam EB generates one or more total reflections in the light guide plate 120 along a second direction D2, and then leaves the light guide plate 120 through a light exiting surface 126 opposite to the light entrance surface 124. In other embodiments, the optical sensing module 100 further includes optical grating structures (not shown). The optical grating structures, for example, are respectively disposed at two ends of a surface 122 of the light guide plate 120. The light source 110 is, for example, disposed at the first side S1 of the light guide plate 120. Therefore, the exciting beam EB enters the light guide plate 120 through the optical grating structure at one end of the light guide plate 120, generates one or more total reflections in the light guide plate 120 along the second direction D2, and then leaves the light guide plate 120 through the optical grating structure at the other end of the light guide plate 120, but the invention is not limited thereto.

Referring to FIG. 1 again, when the exciting beam EB enters the light guide plate 120, at least one portion of the exciting beam EB is transmitted to the sample 50 through the portion of the surface 122 of the light guide plate 120 exposed by the holes H. That's to say, bottoms of the holes H are illuminated by the exciting beam EB. The sample 50 is excited by the exciting beam EB and emits a signal beam SB. A wavelength range of the signal beam SB is different from a wavelength range of the exciting beam EB. The signal beam SB is, for example, a fluorescent beam, but the invention is not limited thereto. The filter layer 150 is adapted to filter the exciting beam EB and allow the signal beam SB to pass through. The signal beam SB in a scattering way passes through the light converging layer 140 and the filter layer 150 in an order and travels to the sensors 160. To be more specific, the signal beam SB sequentially passes through the light guide plate 120, the second cladding layer 180, the light converging layer 140, the filter layer 150, and the passivation layer 170 and travels to the sensors 160. The sensors 160 convert the signal beam SB into electrical signals. A processor (not shown) in the optical sensing module 100 analyzes information of the sample 50 based on the electrical signals. The characteristic of the sample 50 is, for example, the ingredient of the sample 50, but the invention is not limited thereto.

Due to above-mentioned configuration, in the optical sensing module 100 provided in the embodiment of the invention, the signal beam SB passes through the light converging layer 140 and the filter layer 150 to the sensors 160 in an order. The light converging layer 140 provides a converging function between the light guide plate 120 and the filter layer 150, and the filter layer 150 provides a filtering function before the signal beam SB reaches the sensors 160. The light intensity of the signal beam SB can be further improved, and the noise can be filtered. To be more specific, the sensors 160 receive most of the converged signal beam SB due to the converging function provided by the light converging layer 140, and therefore the sensitivity of the optical sensing module 100 can be improved. The SNR of the optical sensing module 100 can be further improved due to the filtering function provided by the filter layer 150. Therefore, the optical sensing module 100 provided in the present embodiment of the invention has high sensitivity and high SNR.

On the other hand, when a portion of the exciting beam EB is transmitted to a portion of a surface 128 of the light guide plate 120, light scattering phenomenon occurs. The filter layer 150 is an interference filter layer which has a better filtering function when light beams are incident to the filter layer 150 at a small light incident angle. The scattered exciting beam EB' can be converged by the light converging layer 140, and therefore, a light incident angle of the converged exciting beam EB" to the filter layer 150 is smaller. The converged exciting beam EB" can be filtered by the filter layer 150 more easily, and sensing results of the sensors 160 are less likely to be affected. That is to say, crosstalk phenomenon in the optical sensing module 100 provided in the present embodiment of the invention can be avoided, and the SNR can be further improved.

Furthermore, since the light converging layer 140 and the filter layer 150 are located between the light guide plate 110 and the sensors 160, the converging function provided by the light converging layer 140 may lead to the improvement of the accuracy of the light transmission between the hole H and the sensor 160 and the efficiency of the filtering function provided by the filter layer 150.

It should be noted that parts of the content in the previous embodiments are used in the following embodiments, and repeated description of the same technical content is omitted. The descriptions of the same elements may be found in the previous embodiments and are not repeated hereinafter.

Figure 2:
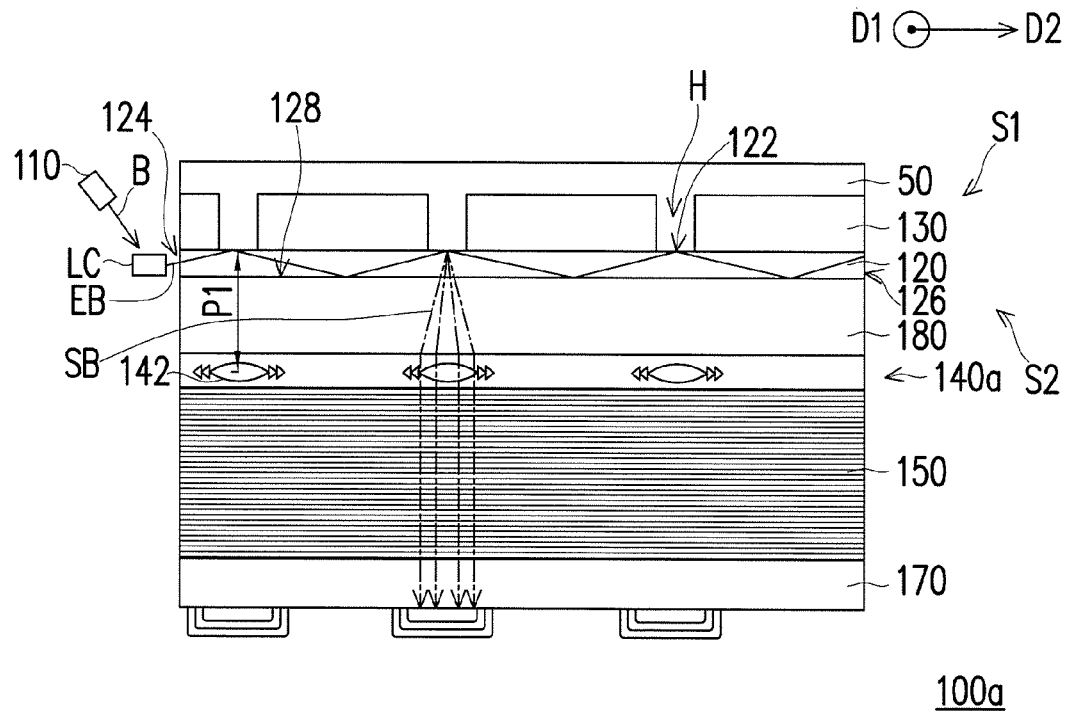
FIG. 2 is a schematic cross-sectional view of an optical sensing module according to another embodiment of the invention.

FIG. 2 is a schematic cross-sectional view of an optical sensing module according to another embodiment of the invention.

Referring to FIG. 2, the optical sensing module 100a in FIG. 2 is similar to the optical sensing module 100 in FIG. 1, while a difference therebetween is that the light converging layer 140a includes a plurality of light converging lenses 142. Positions of the light converging lenses 142 correspond to the positions of the holes H. Each of the light converging lens 142 is located between one of the holes H and the sensor 160. In the embodiment, the light converging lenses 142 are a plurality of Fresnel lenses. In other embodiments, the light converging lenses 142 can be convex lenses or other types of lenses with the light converging function, but the invention is not limited thereto. A distance P1 between a bottom of the hole H and the light converging lens 142 is substantially equal to a focal length of the light converging lens 142. The optical effect of the optical sensing module 100a is similar to that of the optical sensing module 100 in FIG. 1 and thus is not repeated hereinafter. It should be noted that Fresnel lenses with small thickness can achieve a light converging effect, and therefore, the thickness of the optical sensing module 100a can be further reduced compared to a convex lens.

Figure 3A:
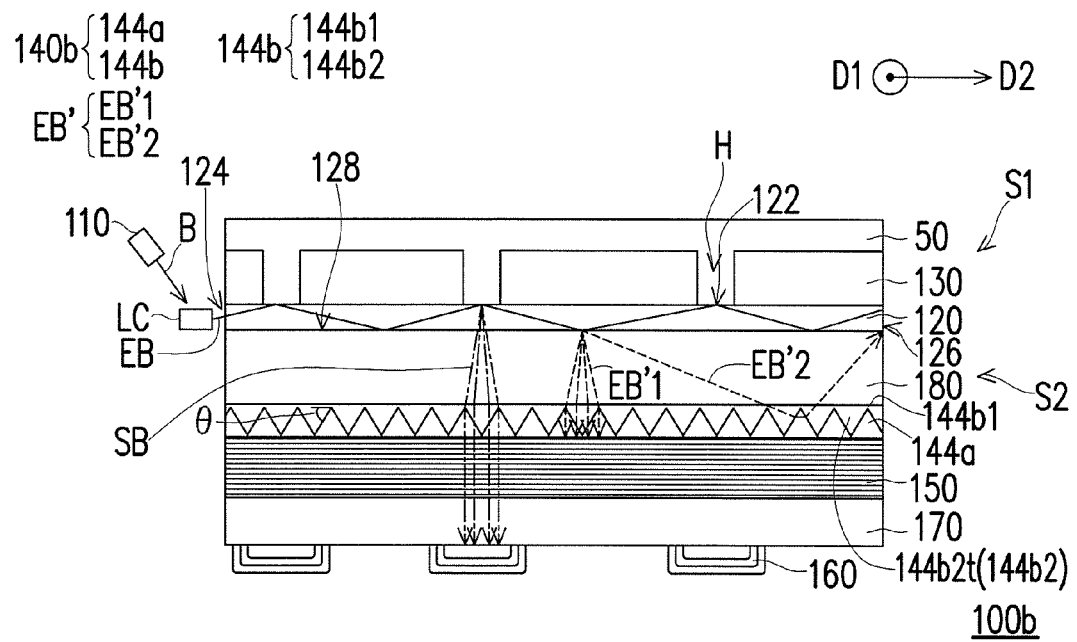
FIG. 3A is a schematic cross-sectional view of an optical sensing module according to another embodiment of the invention.
Figure 3B:
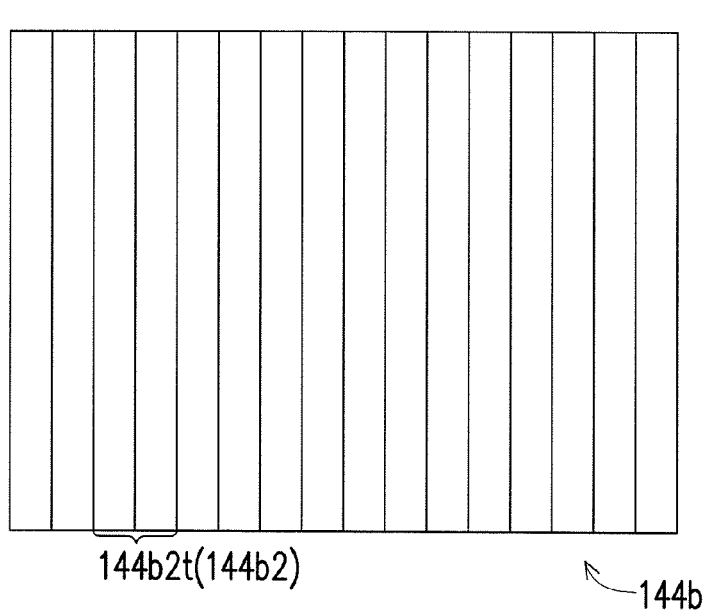
FIG. 3B is a top view of the covering layer in the embodiment of FIG. 3A.
Figure 3C:
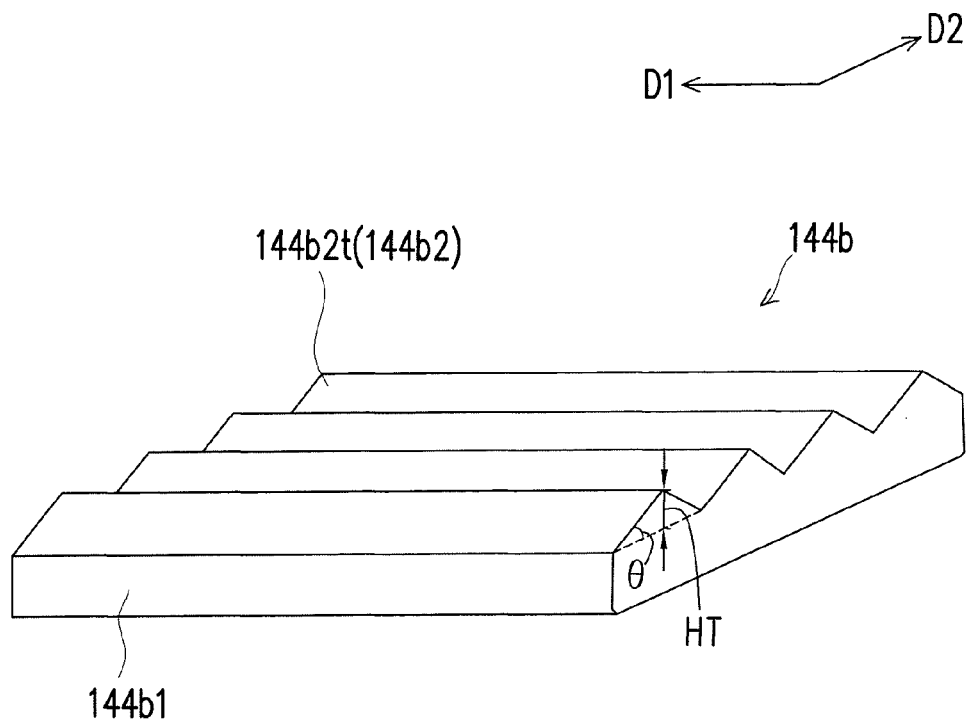
FIG. 3C is an oblique view of the covering layer in the embodiment of FIG. 3A.

FIG. 3A is a schematic cross-sectional view of an optical sensing module according to another embodiment of the invention. FIG. 3B is a top view of the covering layer in the embodiment of FIG. 3A. FIG. 3C is an oblique view of the covering layer in the embodiment of FIG. 3A.

Referring to FIG. 3A to FIG. 3C, the optical sensing module 100b in FIG. 3A is similar to the optical sensing module 100 in FIG. 1, while a difference therebetween is that the light converging layer 140b includes a substrate 144a, and the covering layer 144b. The covering layer 144b includes a base 144b1 and a plurality of light converging structures 144b2. The base 144b1 and the light converging structures 144b2 are integrated formed. The covering layer 144b covers the substrate 144a. To be more specific, the substrate 144a and the light converging structures 144b2 are commentary in shape. The substrate 144a is disposed between the light converging structures 144b2 and the filter layer 150. The light converging structures 144b2 include, for example, a plurality of triangular columnar structures 144b2t. It should be noted that each triangular columnar structure 144b2t has a base angle θ. Preferably, when the base angle θ is smaller than 75 degrees, the light converging layer 140b achieves a good light converging effect. A thickness of the substrate 144a and the base 144b1 is, for example, smaller than or equal to 100 micrometers (μm), but the invention is not limited thereto. A height HT of each triangular columnar structure 144a2t falls in a range of, for example, 0.5 μm to 100 μm, but the invention is not limited thereto. In general, the covering layer 144b can be considered as an inverse prism sheet. The light converging structures 144b2 are arranged on the base 144b1 and face the filter layer 150. In the embodiment, the light converging structures 144b2 include a plurality of triangular columnar structures 144b2t. The triangular columnar structures 144b2t extend in a first direction D1, and the exciting beam EB propagates along a second direction D2. The first direction D1 is perpendicular to the second direction D2. It should be noted that the triangular columnar structures 144a2t are able to converge light in one dimension (i.e., the second direction D2), so as to converge the signal light SB and the exciting beam EB in one dimension.

In detail, the refractive index of the substrate 144a is different to the refractive indexes of the second cladding layer 180 and the covering layer 144b. To be more specific, the refractive index of the covering layer 144b is larger than the refractive indexes of the second cladding layer 180 and the substrate 144a. In the embodiment, a material of the substrate 144a is, for example, silicon nitride ($Si_3N_4$), tantalum pentoxide ($Ta_2O_5$), silicon dioxide ($SiO_2$), aluminium oxide ($Al_2O_3$), or air. The material of the covering layer 144b is, for example, titanium dioxide ($TiO_2$), tantalum pentoxide ($Ta_2O_5$), silicon nitride ($Si_3N_4$), or PMMA. A material of the covering layer 144b is, for example, silicon nitride ($Si_3N_4$), tantalum pentoxide ($Ta_2O_5$), silicon dioxide ($SiO_2$), aluminium oxide ($Al_2O_3$), or air. Table 1 shows the combinations of materials of the second cladding layer 180, the substrate 144a, and the covering layer 144b, but the invention is not limited thereto.

| Group number | second cladding layer 180 | covering layer 144b | substrate 144a |
|---|---|---|---|
| 1 | SiO2 | $TiO_2$ | $Si_3N_4$ |
| 2 | $SiO_2$ | $TiO_2$ | $Ta_2O_5$ |
| 3 | $SiO_2$ | $TiO_2$ | $SiO_2$ |
| 4 | $SiO_2$ | $TiO_2$ | $Al_2O_3$ |
| 5 | $SiO_2$ | $Ta_2O_5$ | $SiO_2$ |
| 6 | $SiO_2$ | $Ta_2O_5$ | $Al_2O_3$ |
| 7 | $SiO_2$ | $Si_3N_4$ | $SiO_2$ |
| 8 | Air | PMMA | Air |
| 9 | Air | $TiO_2$ | $Si_3N_4$ |
| 10 | Air | $TiO_2$ | $Ta_2O_5$ |
| 11 | Air | $TiO_2$ | SiO2 |
| 12 | Air | $TiO_2$ | $Al_2O_3$ |
| 13 | Air | $Ta_2O_5$ | $Si_3N_4$ |
| 14 | Air | $Ta_2O_5$ | $SiO_2$ |
| 15 | Air | $Si_3N_4$ | $SiO_2$ |

In other embodiments, a material of the light guide plate 110 and the light converging layer 140 can be appropriately adjusted, so as to provide a proper light converging function.

Referring to FIG. 3A again, the scattered exciting beam EB' is incident to the light converging layer 140b at different angles. A portion of the scattered exciting beam EB'1 having a smaller scattering angle is converged by the light converging layer 140b, and then the scattered exciting beam EB'1 is filtered by the filter layer 150. A portion of the scattered exciting beam EB'2 having a bigger scattering angle is refracted one or more times by the light converging layer 140b. The optical path of the scattered exciting beam EB'2 is changed and is transmitted along a direction from the light converging layer 140a to the light guide plate 120. Since the scattered exciting beam EB2 is reflected, the sensing results of the sensors 160 are less likely to be affected. Therefore, the SNR of the optical sensing module 100b can be further improved.

Figure 4A:
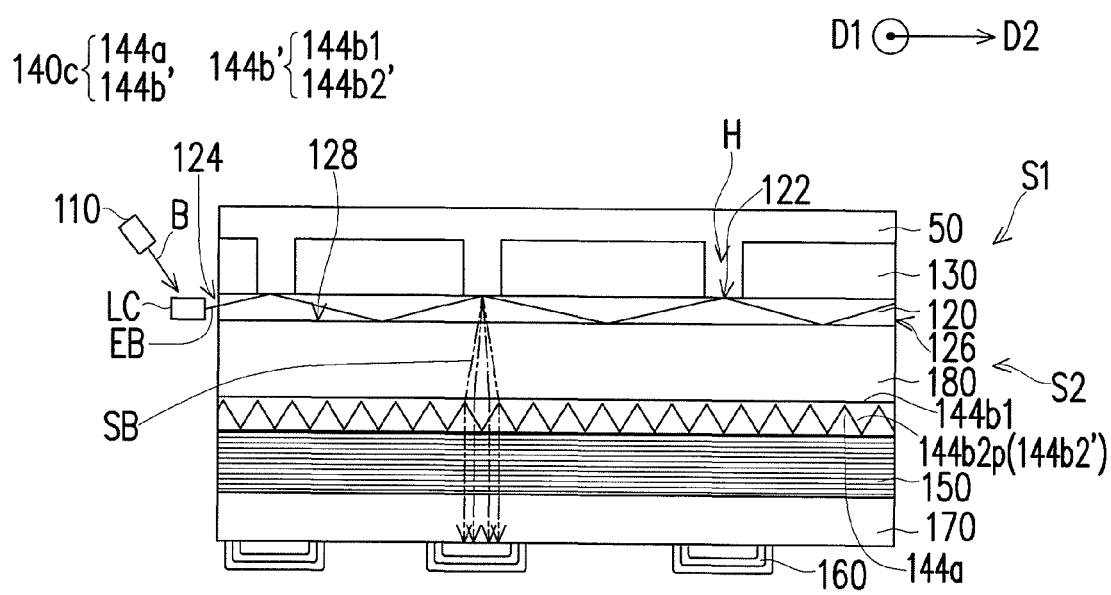
FIG. 4A is a schematic cross-sectional view of an optical sensing module according to another embodiment of the invention.
Figure 4B:
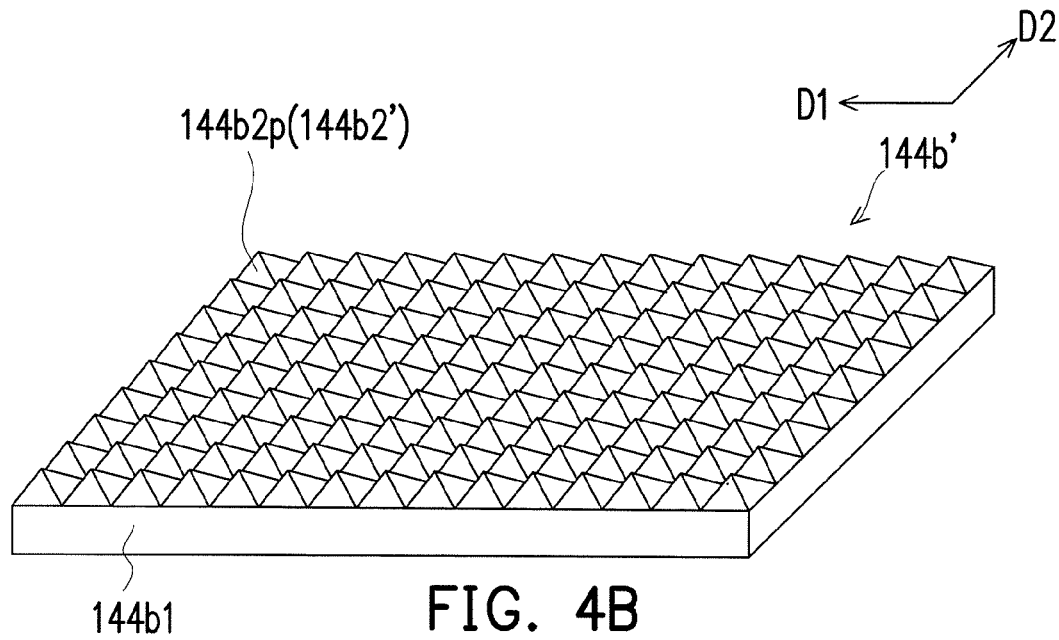
FIG. 4B is an oblique view of the covering layer in the embodiment of FIG. 4A.
Figure 4C:
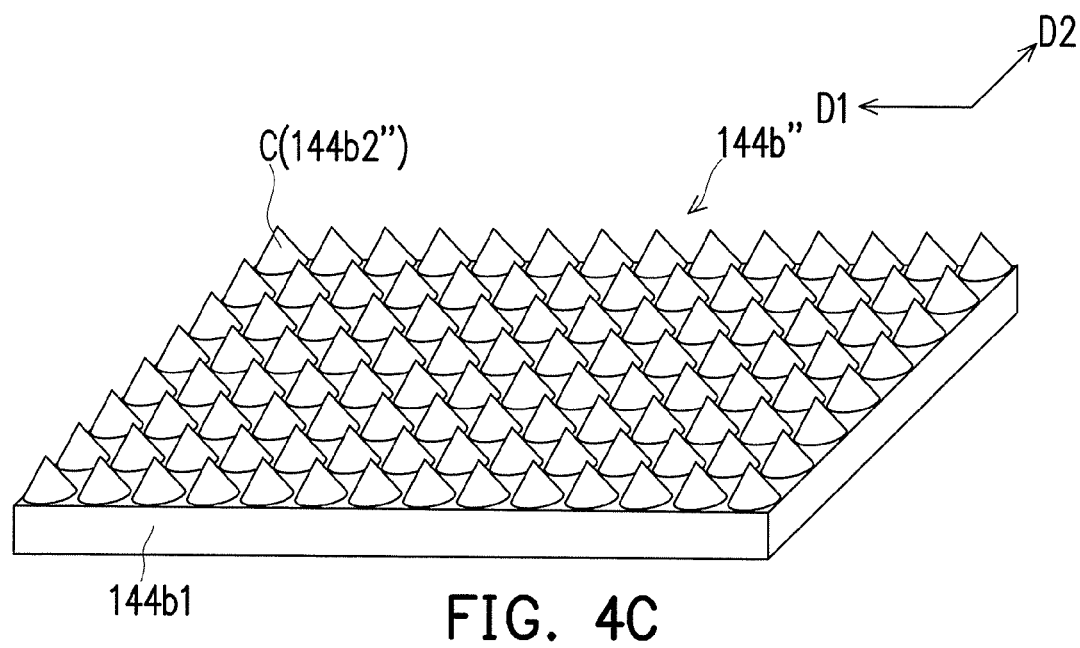
FIG. 4C, FIG. 4D and FIG. 4E are oblique views of covering layers in the different embodiments.
Figure 4D:
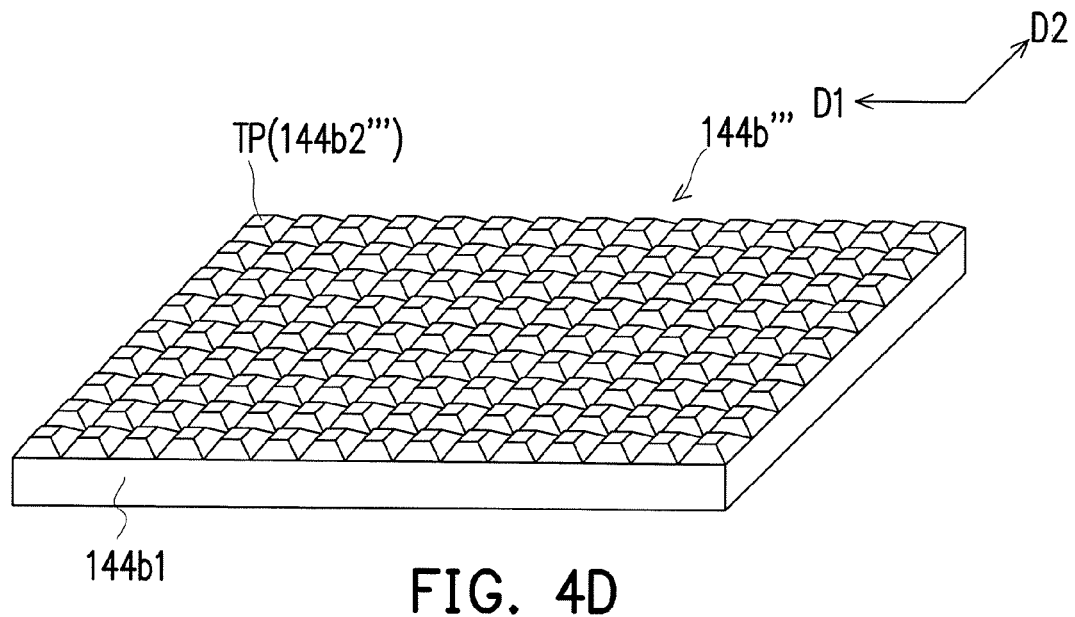
Figure 4E:
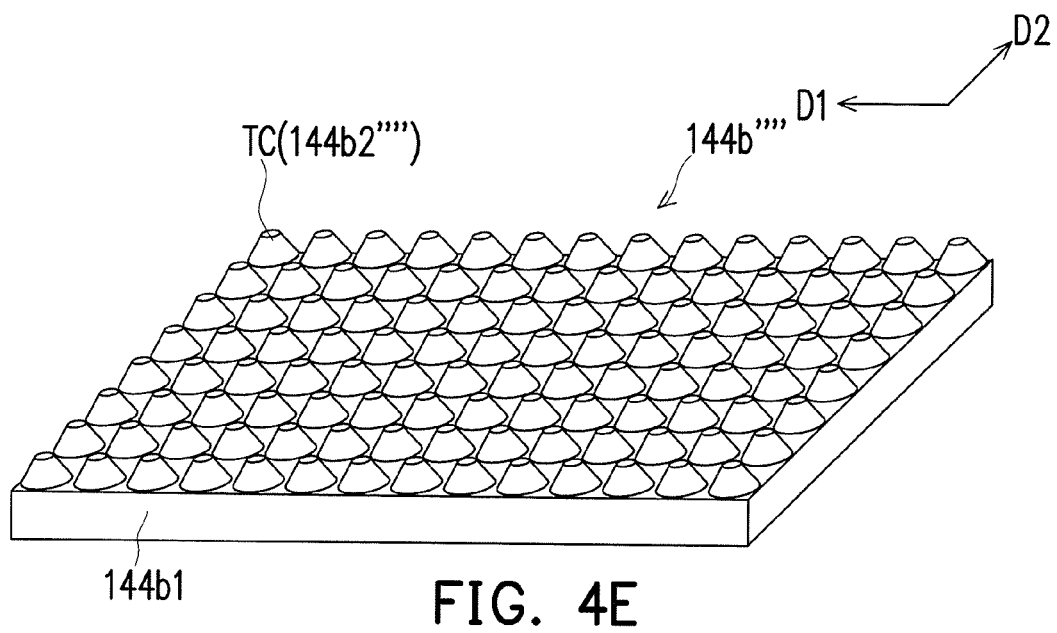

FIG. 4A is a schematic cross-sectional view of an optical sensing module according to another embodiment of the invention. FIG. 4B is an oblique view of the covering layer in the embodiment of FIG. 4A. FIG. 4C, FIG. 4D and FIG. 4E are oblique views of covering layers in the different embodiments.

Referring to the FIG. 4A and FIG. 4B, the optical sensing module 100c in FIG. 4A is similar to the optical sensing module 100b in FIG. 3A, while a difference therebetween is that the light converging structures 144b2' include a plurality of trigonal tapers 144b2p. It should be noted that the ability of converging light of the light converging structures 144b2' is improved when the light converging structures 144b2' include the trigonal tapers 144b2p. The optical performances of the optical sensing module 100c are similar to those of the optical sensing module 100 in FIG. 1 and thus are not repeated hereinafter. Referring to FIG. 4C, FIG. 4D and FIG. 4E, in other embodiments, the light converging structures 144b2" can include a plurality of cones C and a base 144b1 as shown in FIG. 4C. The light converging structures 144b2''' can include a plurality of trapezoidal pillar structures TP and a base 144b1 as shown in FIG. 4D. The light converging structures 144b2"" can include a plurality of trapezoidal cone TC and a base 144b1 as shown in FIG. 4E. It should be noted that when the light converging structures are the cones C, the trapezoidal pillar structures TP or the trapezoidal cones TC, the performances of the sensitivity and SNR are better.

Figure 5A:
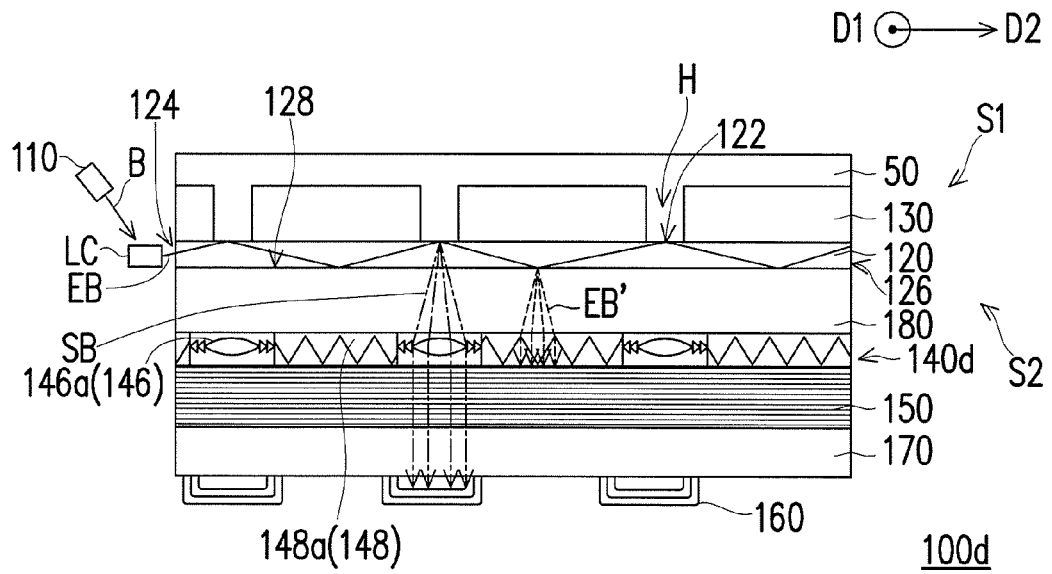
FIG. 5A is a schematic cross-sectional view of an optical sensing module according to another embodiment of the invention.
Figure 5B:
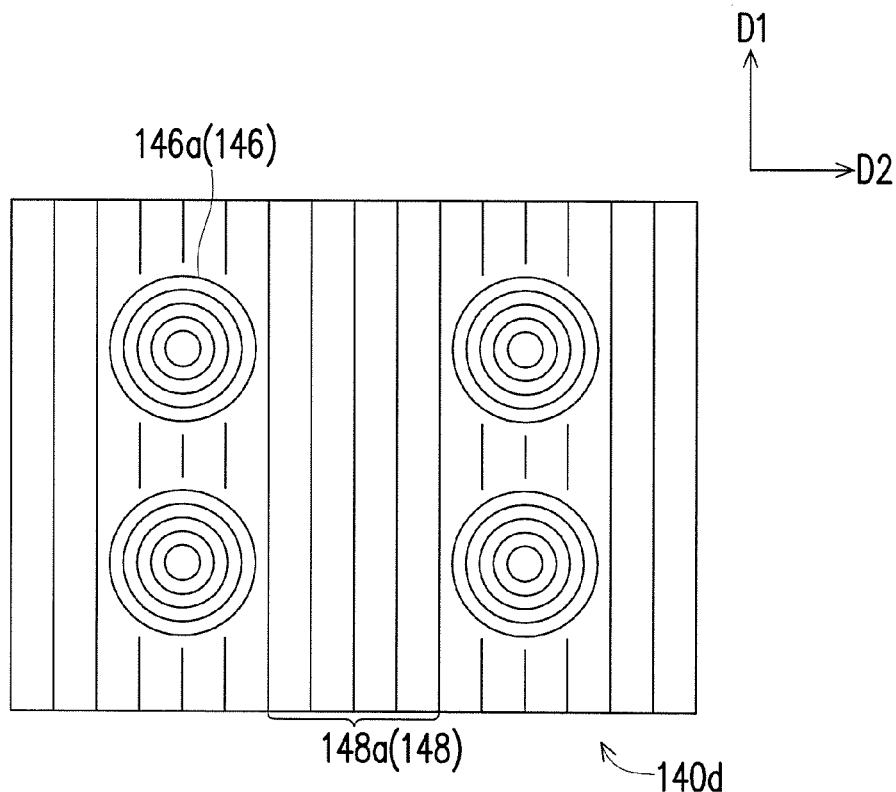
FIG. 5B is a top view of the light converging layer in the embodiment of FIG. 5A.

FIG. 5A is a schematic cross-sectional view of an optical sensing module according to another embodiment of the invention. FIG. 5B is a top view of the light converging layer in the embodiment of FIG. 5A.

Referring to FIG. 5A and FIG. 5B, the optical sensing module 100d in FIG. 5A is similar to the optical sensing module 100 in FIG. 1, while a difference therebetween is that the light converging layer 140d includes a plurality of first light functional elements 146 and a plurality of second light functional elements 148. Positions of the first light functional elements 146 correspond to the positions of the holes H. To be more specific, the first light functional element is located between the hole H and the sensor 160. Any one of the first light functional elements 146 is located between two adjacent second light functional elements 148. To be more specific, the first light functional elements 146 include a plurality of first light converging elements 146a, and the second light functional elements 148 include a plurality of second light converging elements 148a. The first light converging elements 146a are different from the second light converging elements 148a. To be more specific, the first light converging elements 146a include a plurality of Fresnel lenses. The second light converging elements 148a include a plurality of reverse prism sheets. It should be noted that the invention is not limited by a combination of the Fresnel lenses and the reverse prism sheets, and the first light converging elements 146a and the second light converging elements 148a can be replaced with other types of optical lenses elements with the light converging function. The optical performances of the optical sensing module 100d are similar to those of the optical sensing module 100 in FIG. 1 and thus are not repeated hereinafter.

Figure 6A:
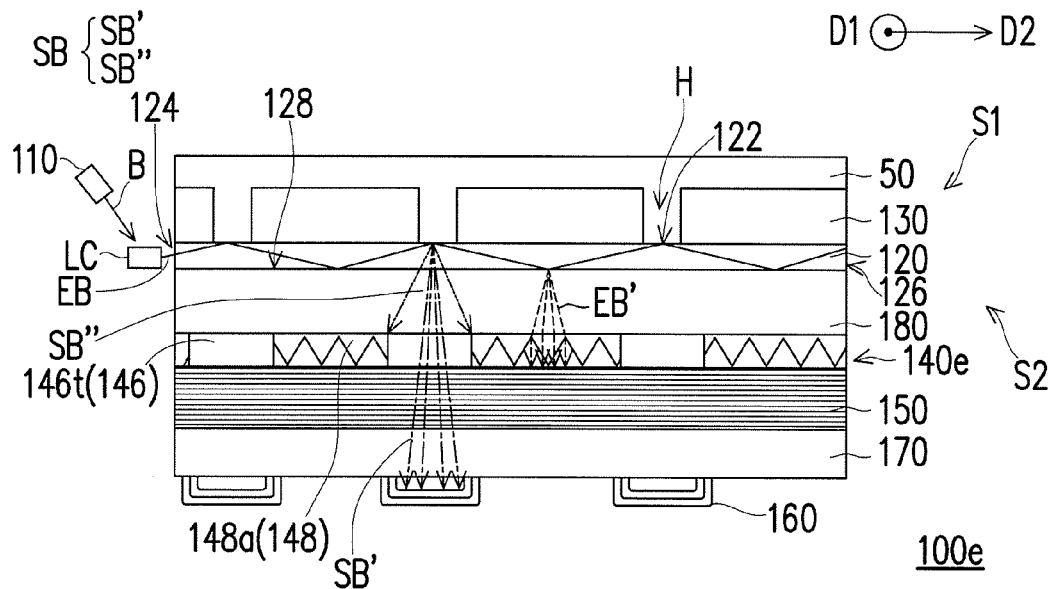
FIG. 6A is a schematic cross-sectional view of an optical sensing module according to another embodiment of the invention.
Figure 6B:
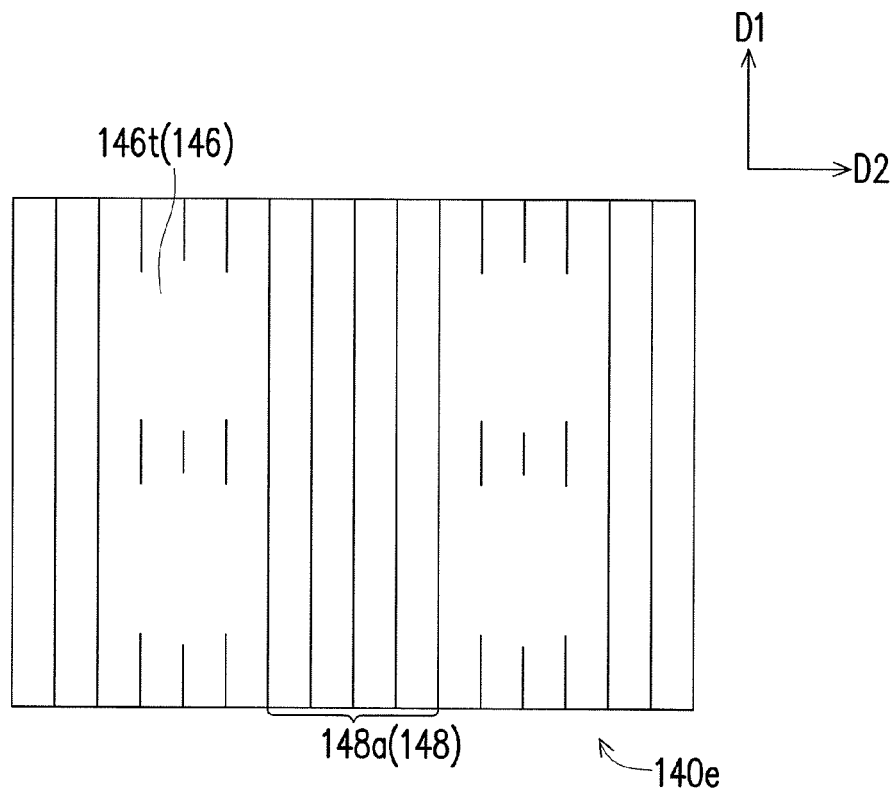
FIG. 6B is a top view of the light converging layer in the embodiment of FIG. 6A.

FIG. 6A is a schematic cross-sectional view of an optical sensing module according to another embodiment of the invention. FIG. 6B is a top view of the light converging layer in the embodiment of FIG. 6A.

Referring to FIG. 6A and FIG. 6B, the optical sensing module 100e in FIG. 6A is similar to the optical sensing module 100 in FIG. 1, while a difference therebetween is that the first light functional elements 146 include a plurality of light transmitting elements 146t, and the second light functional elements 148 include a plurality of second light converging elements 148a. In the embodiment, the signal beam SB' having a smaller scattering angle sequentially passes through the light guide plate 120, the second cladding layer 180, the light transmitting elements 146t, the filter layer 150 and travels to the sensors 160. The signal beam SB" having a bigger scattering angle is converged by the second light converging elements 148a. Therefore, crosstalk phenomenon between two adjacent sensors 160 can be avoided. In the embodiment, the optical sensing module 100e can reach an effect similar to the effect of converging light due to the configuration of the light transmitting elements 146t and the second light converging elements 148a. Furthermore, the optical sensing module 100e can filter the excitation light EB' outside the sensing area easier.

Figure 7:
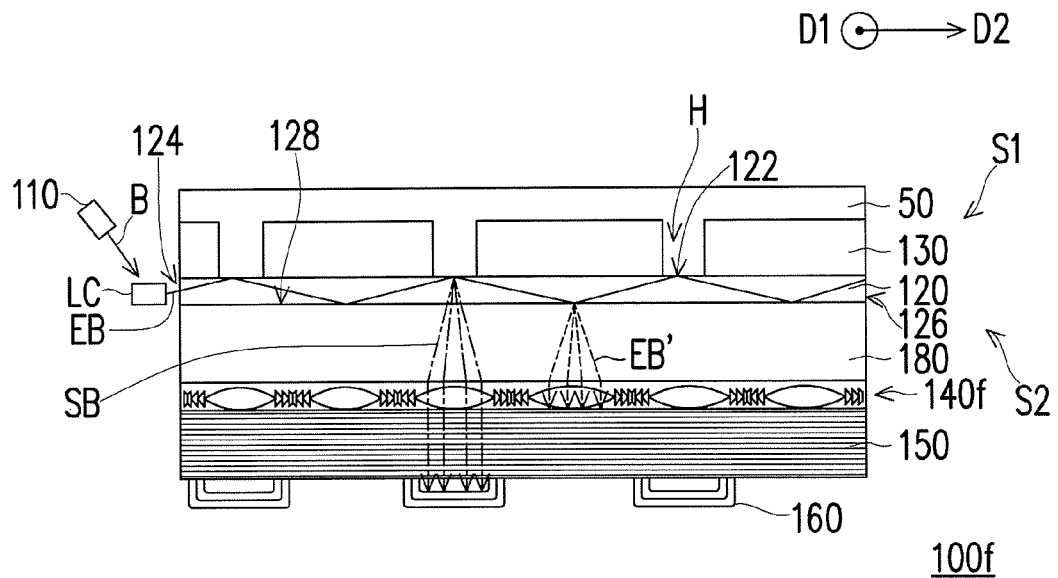
FIG. 7 is a schematic cross-sectional view of an optical sensing module according to another embodiment of the invention.

FIG. 7 is a schematic cross-sectional view of an optical sensing module according to another embodiment of the invention.

Referring to FIG. 7, the optical sensing module 100f in FIG. 7 is similar to the optical sensing module 100d in FIG. 5A, while a difference therebetween is that first light converging elements 146a and the second light converging elements 148a are the same. The first light converging elements 146a and the second light converging elements 148a include, for example, a plurality of Fresnel lenses. In other embodiments, first light converging elements 146a and the second light converging elements 148a can include other types of optical lenses elements with the light converging function, and the invention is not limited thereto. The optical performances of the optical sensing module 100e are similar to those of the optical sensing module 100 in FIG. 1 and thus are not repeated hereinafter.

Figure 8:
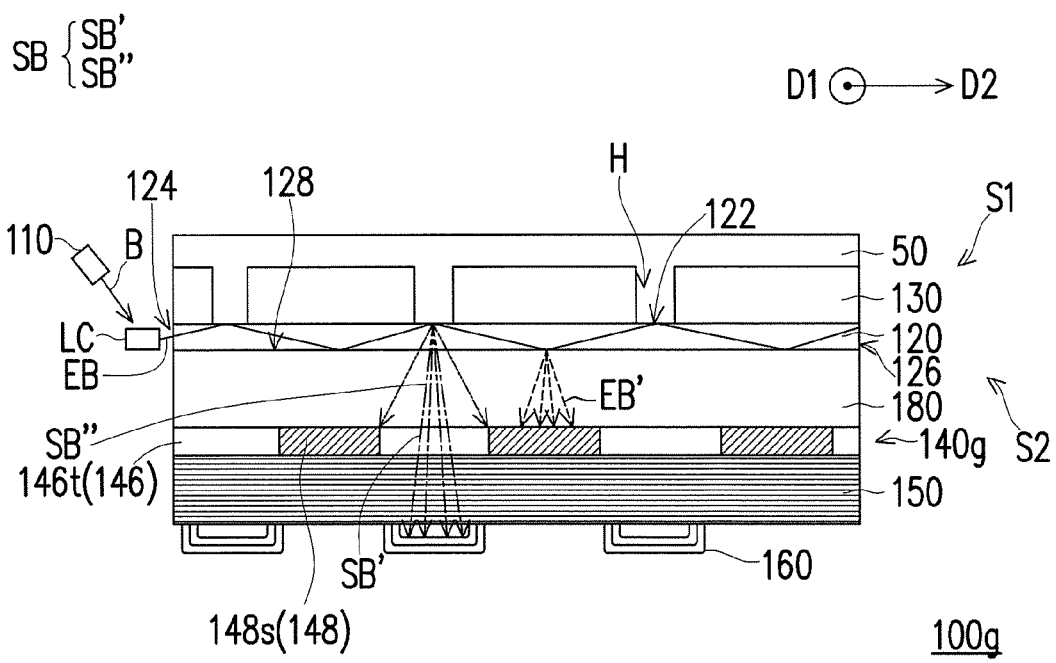
FIG. 8 is a schematic cross-sectional view of an optical sensing module according to another embodiment of the invention.

FIG. 8 is a schematic cross-sectional view of an optical sensing module according to another embodiment of the invention.

Referring to FIG. 8, the optical sensing module 100g in FIG. 8 is similar to the optical sensing module 100d in FIG. 5A, while a difference therebetween is that the first light functional elements 146 include a plurality of light transmitting elements 146t, and the second light functional elements 148 include a plurality of light shielding elements 148s. In detail, the light transmitting elements 146t cover one portion of a surface of the filter layer 150, and the light shielding elements 148s cover the other portion of the surface of the filter layer 150. In the embodiment, the signal beam SB' having a smaller scattering angle sequentially passes through the light guide plate 120, the second cladding layer 180, the light transmitting elements 146t, the filter layer 150 and travels to the sensors 160. The signal beam SB" having a bigger scattering angle is shielded by the light shielding elements 148s. In the embodiment, the optical sensing module 100g can reach an effect similar to the effect of converging light due to the configuration of the light transmitting elements 146t and the light shielding elements 148s. The light shielding elements 148s can shield a portion of the scattered exciting beam EB', and therefore the sensing results of the sensors 160 are less likely to be affected. In the embodiment, the thicknesses of the light shielding elements 148s falls in a range of, for example, 10 nm to 50 μm, but the invention is not limited thereto. The light shielding elements 148s are, for example, reflective elements. A material of the light shielding elements 148s is, for example, Ag, Cu, Au, Ti, Ni, Al, Cr or other metal, but the invention is not limited thereto.

Figure 9:
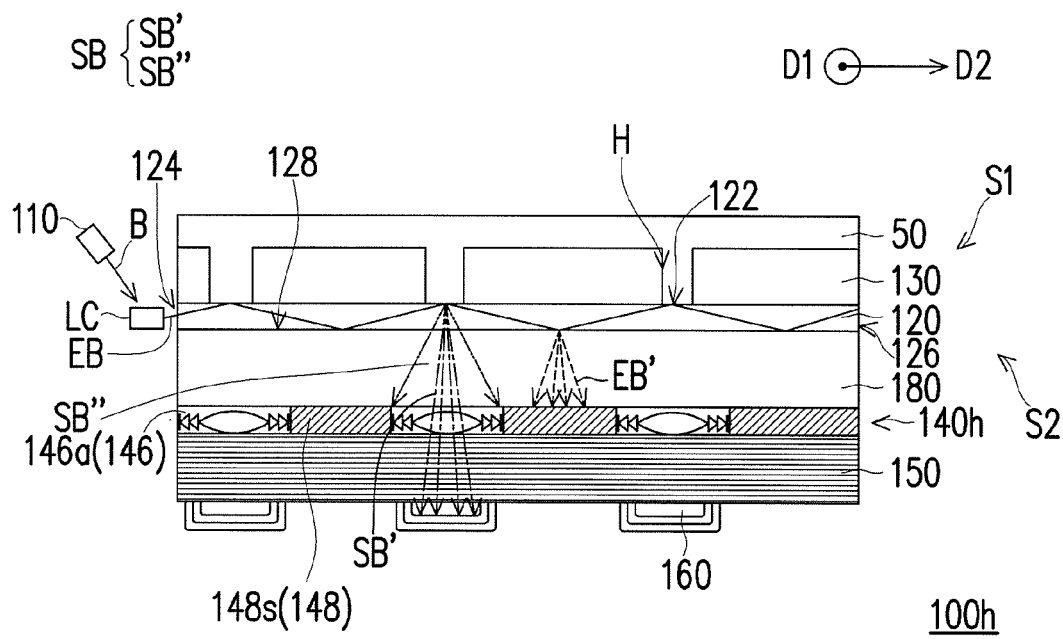
FIG. 9 is a schematic cross-sectional view of an optical sensing module according to another embodiment of the invention.

FIG. 9 is a schematic cross-sectional view of an optical sensing module according to another embodiment of the invention.

Referring to FIG. 9, the optical sensing module 100h in FIG. 9 is similar to the optical sensing module 100d in FIG. 5A, while a difference therebetween is that the first light functional elements 146 include a plurality of first light converging elements 146a, and the second light functional elements 148 include a plurality of light shielding elements 148s. In the embodiment, the signal beam SB' having a smaller scattering angle sequentially passes through the light guide plate 120, the second cladding layer 180, the first light converging elements 146a, the filter layer 150 and travels to the sensors 160. The signal beam SB' is further converged by the first light converging elements 146a. The signal beam SB" having a bigger scattering angle is shielded by the light shielding elements 148s. Meanwhile, the light shielding elements 148s can shield a portion of the scattered exciting beam EB', and therefore the sensing results of the sensors 160 are less likely to be affected.

Figure 10:
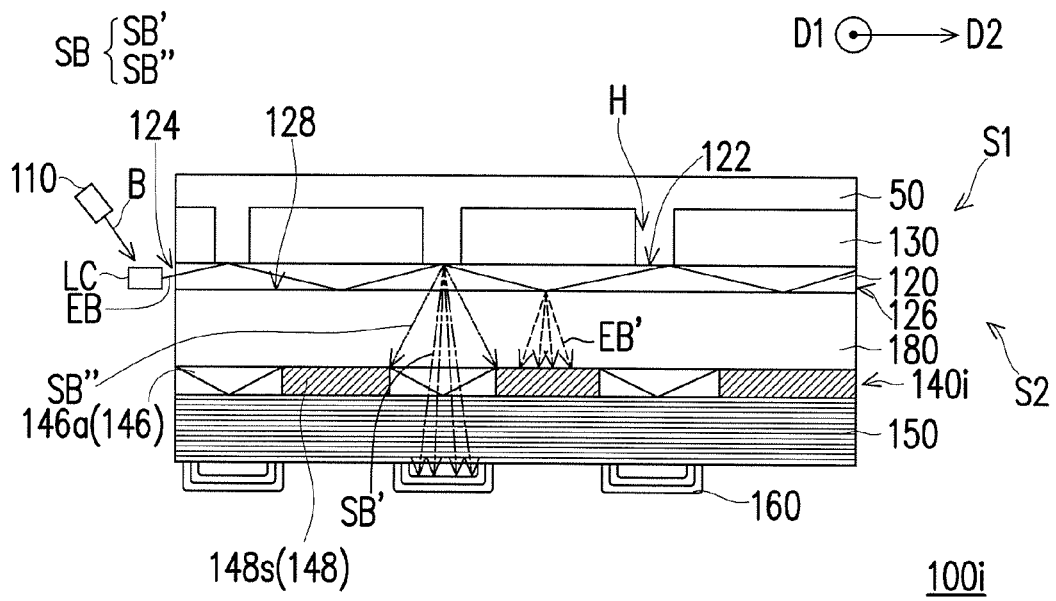
FIG. 10 is a schematic cross-sectional view of an optical sensing module according to another embodiment of the invention.

FIG. 10 is a schematic cross-sectional view of an optical sensing module according to another embodiment of the invention.

Referring to FIG. 10, the optical sensing module 100i in FIG. 10 is similar to the optical sensing module 100h in FIG. 9, while a difference therebetween is that the first light converging elements 146a are, for example, triangular prisms. In other embodiments, the first light converging elements 146 include a plurality of pyramids, cones, a plurality of trapezoidal tapers, or a plurality of trapezoidal cones.

Figure 11:
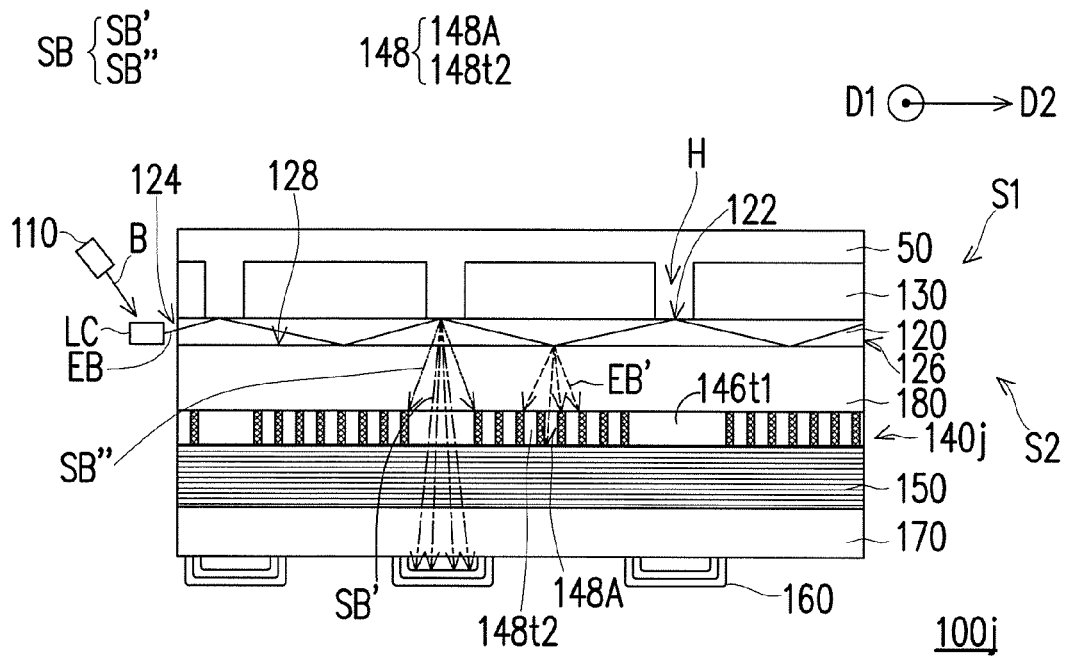
FIG. 11 is a schematic cross-sectional view of an optical sensing module according to another embodiment of the invention.

FIG. 11 is a schematic cross-sectional view of an optical sensing module according to another embodiment of the invention.

Referring to FIG. 11, the optical sensing module 100j in FIG. 11 is similar to the optical sensing module 100d in FIG. 5A, while a difference therebetween is that the first light functional elements 146 include a plurality of first light transmitting elements 146*t*1, and the second light functional elements 148 include a plurality of light absorbing elements 148A and a plurality of second light transmitting elements 148*t*2. The first light transmitting elements 146*t*1, the light absorbing elements 148A, and the second light transmitting elements 148*t*2 are arranged in the second direction D2. In the embodiment, the signal beam SB' having a smaller scattering angle sequentially passes through the light guide plate 120, the second cladding layer 180, the first light transmitting elements 146*t*1, the filter layer 150 and travels to the sensors 160. The signal beam SB" having a bigger scattering angle is absorbed by the light absorbing elements 148A. Therefore, crosstalk phenomenon between two adjacent sensors 160 can be avoided. The optical sensing module 100*j* can reach an effect similar to the effect of converging light due to the configuration of the first light transmitting elements 146*t*1, the light absorbing elements 148A, and the second light transmitting elements 148*t*2. On the other hand, one portion of the scattered exciting beam EB' (with larger incident angle) is absorbed by the light absorbing elements 148A, and the other portion of the exciting beam EB' (with smaller incident angle) passes through the second light transmitting elements 148*t*2 and is filtered by the filter layer 150. Therefore, the sensing results of the sensors 160 are less likely to be affected.

Figure 12:
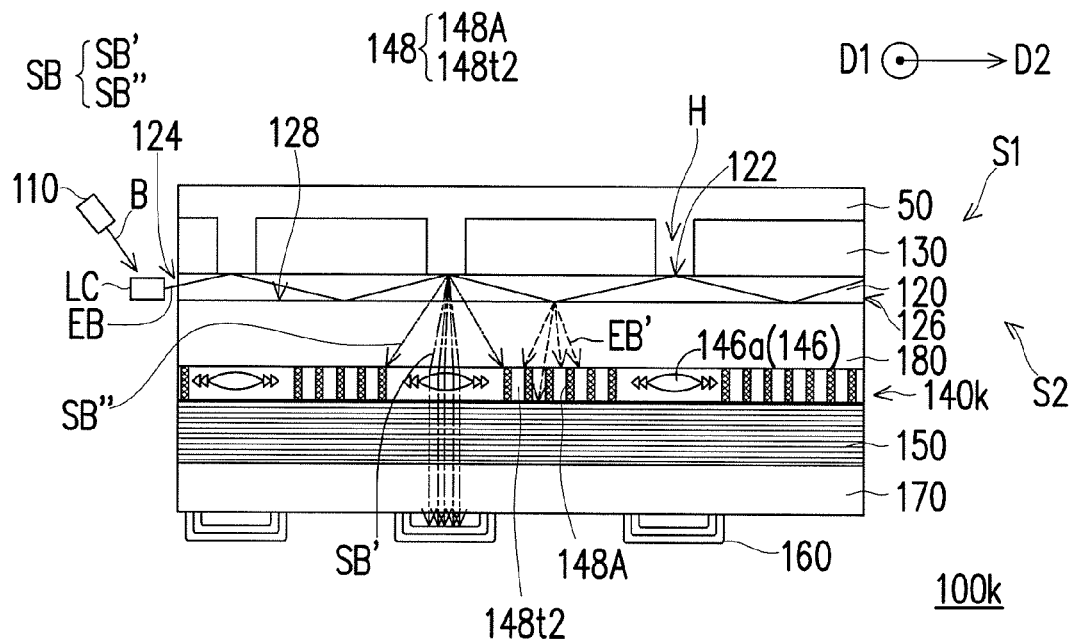
FIG. 12 is a schematic cross-sectional view of an optical sensing module according to another embodiment of the invention.

FIG. 12 is a schematic cross-sectional view of an optical sensing module according to another embodiment of the invention.

Referring to FIG. 12, the optical sensing module 100*k* in FIG. 12 is similar to the optical sensing module 100*j* in FIG. 11, while a difference therebetween is that the first light functional elements 146 include a plurality of first light converging elements 146*a*, and the second light functional elements 148 include a plurality of light absorbing elements 148A and a plurality of second light transmitting elements 148*t*2. In the embodiment, the signal beam SB is converged by the light converging elements 146*a* and travels to the sensors 160. On the other hand, one portion of the scattered exciting beam EB' is absorbed by the light absorbing elements 148A, and the other portion of the exciting beam EB' passes through the second light transmitting elements 148*t*2 and is filtered by the filter layer 150. Therefore, the sensing results of the sensors 160 are less likely to be affected.

Figure 13:
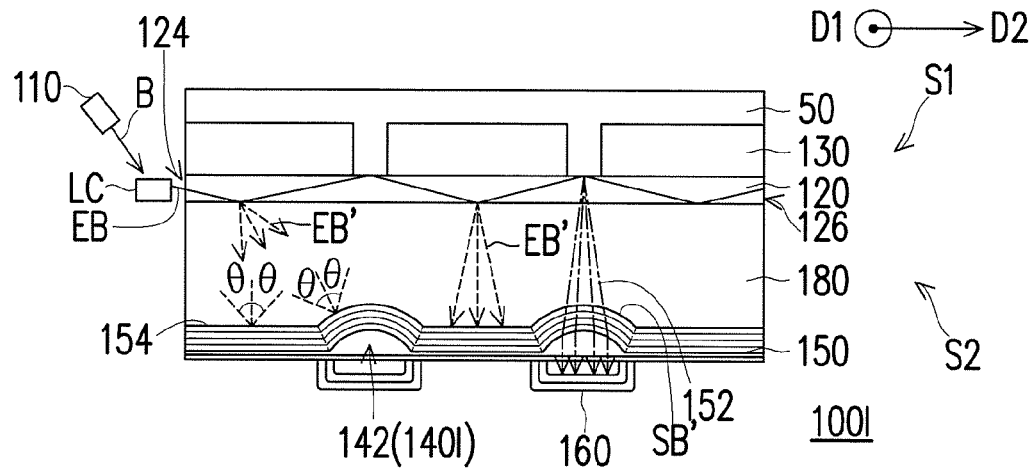
FIG. 13 is a schematic cross-sectional view of an optical sensing module according to another embodiment of the invention.

FIG. 13 is a schematic cross-sectional view of an optical sensing module according to another embodiment of the invention.

Referring to FIG. 13, the optical sensing module 100*l* in FIG. 13 is similar to the optical sensing module 100 in FIG. 1, while a difference therebetween is that the light converging layer 140*l* is disposed between the filter layer 150 and the sensors 160. In detail, the light converging layer 140*j* includes a plurality of the light converging lenses 142. The light converging lenses 142 are, for example, micro lenses. Positions of the light converging lenses 142 correspond to the positions of the holes H and the positions of the sensors 160. The filter layer 150 is disposed to have the same shape as the light converging lenses 142, so as to form a plurality of convex areas 152 in the filter layer 150. The areas in the filter layer 150 except the convex areas 152 are flat areas 154. In the embodiment, the signal beam SB passes through the light converging layer 140*j* and the filter layer 150 in an order and travels to the sensors 160. To be more specific, the signal beam SB sequentially passes through the filter layer 150 and the light converging layer 140*j* and travels to the sensors 160.

In the embodiment, the filter layer 150 is, for example, an interference filter layer. The interference filter layer performs a better filtering function when the incident light beams are incident to the interference filter layer at a smaller light incident angle. In other words, the interference filter layer has different filtering abilities at different light incident angles. For example, in the embodiment, the filter layer 150 can filter the light beams incident to the filter layer 150 at an incident angle in an angle range composed of the positive angle θ and the negative angle −θ relative to the normal direction of the filter layer 150. Since the normal directions are different at different places of the convex areas 152, the filter layer 150 can filter the scattered exciting beam EB' having a bigger scattering angle. Therefore, the sensing results of the sensors 160 are less likely to be affected.

Figure 14:
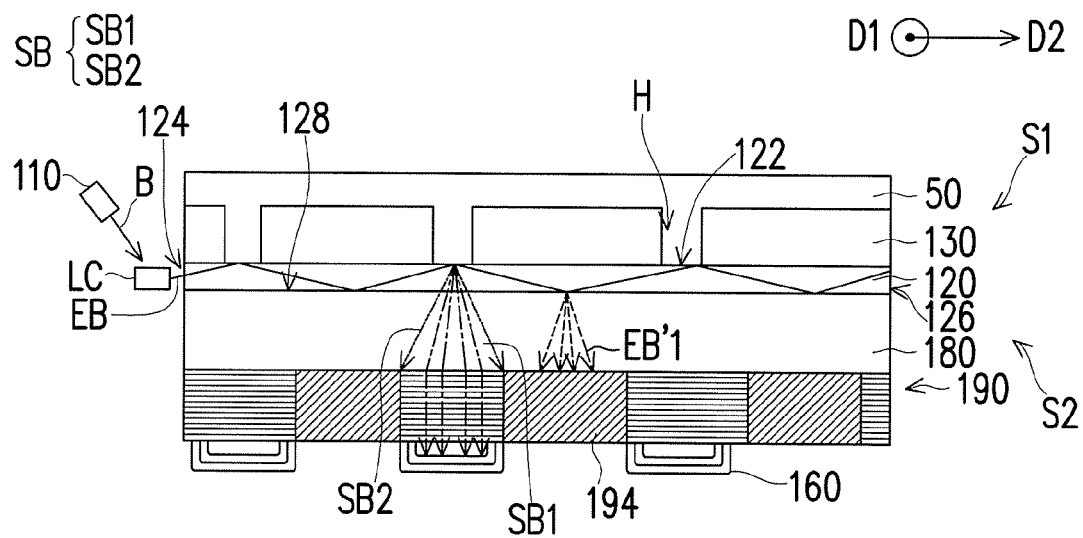
FIG. 14 is a schematic cross-sectional view of an optical sensing module according to another embodiment of the invention.

FIG. 14 is a schematic cross-sectional view of an optical sensing module according to another embodiment of the invention.

Referring to the FIG. 14, in the embodiment, the optical sensing module 100*m* includes a light source 110, a light guide plate 120, a first cladding layer 130, a noise-reduction layer 190, a plurality of sensors 160, and a second cladding layer 180.

The light source 110 is configured to provide an exciting beam EB. The light guide plate 120 having a first side S1 and a second side S2 opposite to each other. The first cladding layer 130 is disposed at the first side S1 of the light guide plate 120. The second cladding layer 180 is disposed at the second side S2 of the light guide plate 120. The first cladding layer 130 has a plurality of holes H. The holes H expose a portion of a surface 122 of the light guide plate 120. The sample 50 is placed in at least one of the holes H. The noise-reduction layer 190 includes a plurality of filter elements 192 and a plurality of light shielding elements 194. Positions of the filter elements 192 correspond to the positions of the holes H. Any one of the light shielding elements 194 is located between two adjacent filter elements 192. The filter elements 192 are, for example, interference filter layers, but the invention is not limited thereto. Positions of the sensors 160 correspond to the positions of the holes H. The noise-reduction layer 190 is disposed between the sensors 160 and the light guide plate 120. After the exciting beam EB enters the light guide plate 120, at least one portion of the exciting beam EB is transmitted to the sample 50 through the portion of the surface 122 of the light guide plate 120 exposed by the holes H. The sample 50 is excited by the exciting beam EB to emit a signal beam SB. A first portion SB1 of the signal beam SB passes through at least one of the filter elements 192 and travels to the sensor 160. A second portion SB2 of the signal beam SB is shielded by at least one of the light shielding elements 194.

To be more specific, the first portion SB1 of the signal beam SB has, for example, a smaller light scattering angle. The second portion SB2 of the signal beam SB has, for example, a bigger light scattering angle. In the embodiment, the first portion SB1 of the signal beam SB is filtered by the filter elements 192. On the other hand, the second portion SB2 of the signal beam SB is shielded by the light shielding elements 194. The optical sensing module 100*k* performs a filtering function and a light converging function by the noise-reduction layer 190 and also has a small thickness. Therefore, the optical sensing module 100*k* has high sensitivity, high SNR, and small thickness.

In view of the forgoing, in the optical sensing module provided in the embodiments of the invention, the signal beam passes through the light converging layer in an order and travels to the sensors. The light converging layer performs a converging function, and the filter layer performs a filtering function. Hence, the optical sensing module provided in the embodiments of the invention has high sensitivity and high SNR. Next, a portion of the exciting beam can be converged by the light converging layer, and the sensing results of the sensors are less likely to be affected. That is to say, crosstalk phenomenon in the optical sensing module provided in the embodiments of the invention can be avoided. Furthermore, since the light converging layer and the filter layer are located between the light guide plate and the sensors, the converging function provided by the light converging layer can improve the accuracy of the light transmission between the holes and the sensor and the efficiency of the filtering function provided by the filter layer.

On the other hand, in the optical sensing module provided in the embodiments of the invention, the first portion of the signal beam is filtered by the filter elements, and the second portion of the signal beam is shielded by the light shielding elements. The optical sensing module performs a filtering function and a light converging function by the noise-reduction layer and also has a small thickness. Therefore, the optical sensing module provided in the embodiments of the invention has high sensitivity, high SNR, and small thickness.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. An optical sensing module, configured to detect a characteristic of a sample, the optical sensing module comprising:
   a light source, configured to provide an exciting beam;
   a light guide plate, having a first side and a second side opposite to each other;
   a first cladding layer, disposed at the first side of the light guide plate, the first cladding layer having a plurality of holes, the holes exposing a portion of a surface of the light guide plate, wherein the sample is placed in at least one of the holes;
   a light converging layer, disposed at the second side of the light guide plate;
   a filter layer; and
   a plurality of sensors, positions of the sensors corresponding to positions of the holes,
   wherein after the exciting beam enters the light guide plate, at least one portion of the exciting beam is transmitted to the sample through the portion of the surface of the light guide plate exposed by the holes, the sample is excited by the exciting beam to emit a signal beam, and the signal beam passes through the light converging layer and the filter layer in an order and travels to the sensors.

2. The optical sensing module according to claim 1, wherein the light converging layer comprises a plurality of light converging lenses, and positions of the light converging lenses correspond to the positions of the holes.

3. The optical sensing module according to claim 1, wherein the light converging layer comprises a substrate and a covering layer, the covering layer comprises a base and a plurality of light converging structures, the light converging structures are arranged on the base and face the filter layer, and the covering layer covers the substrate.

4. The optical sensing module according to claim 3, wherein the light converging structures comprise a plurality of triangular columnar structures, the triangular columnar structures extend in a first direction, and the exciting beam propagates along a second direction, wherein the first direction is perpendicular to the second direction.

5. The optical sensing module according to claim 3, wherein the light converging structures comprise a plurality of trigonal tapers, a plurality of cones, a plurality of trapezoidal pillar structures, or a plurality of trapezoidal cones.

6. The optical sensing module according to claim 1, wherein the light converging layer comprises a plurality of first light functional elements and a plurality of second light functional elements, wherein positions of the first light functional elements correspond to positions of the second light functional elements, and any one of the first light functional elements is located between two adjacent second light functional elements of the second light functional elements.

7. The optical sensing module according to claim 6, wherein the first light functional elements comprise a plurality of first light converging elements, and the second light functional elements comprise a plurality of second light converging elements.

8. The optical sensing module according to claim 6, wherein the first light functional elements comprise a plurality of light transmitting elements, and the second light functional elements comprise a plurality of light shielding elements.

9. The optical sensing module according to claim 6, wherein the first light functional elements comprise a plurality of first light converging elements, and the second light functional elements comprise a plurality of light shielding elements.

10. The optical sensing module according to claim 6, wherein the first light functional elements comprise a plurality of first light transmitting elements, and the second light functional elements comprise a plurality of light absorbing elements and a plurality of second light transmitting elements.

11. The optical sensing module according to claim 6, wherein the first light functional elements comprise a plurality of light transmitting elements, and the second light functional elements comprise a plurality of second light converging elements.

12. The optical sensing module according to claim 1, wherein the light converging layer is disposed between the light guide plate and the filter layer.

13. The optical sensing module according to claim 1, wherein the light converging layer is disposed between the filter layer and the sensors.

14. The optical sensing module according to claim 1, further comprising a passivation layer disposed between the filter layer and the sensors.

15. The optical sensing module according to claim 1, further comprising a second cladding layer disposed between the light guide plate and the light converging layer.

16. The optical sensing module according to claim 1, wherein the filter layer comprises an absorption filter layer or an interference filter layer.

17. An optical sensing module, configured to detect a characteristic of a sample, the optical sensing module comprising:
   a light source, configured to provide an exciting beam;
   a light guide plate, having a first side and a second side opposite to each other;
   a first cladding layer, disposed at the first side of the light guide plate, the first cladding layer having a plurality of holes, the holes exposing a portion of a surface of the light guide plate, wherein the sample is placed in at least one of the holes;
a noise-reduction layer, comprising a plurality of filter elements and a plurality of light shielding elements, wherein positions of the filter elements correspond to positions of the holes, and any one of the light shielding elements is located between two adjacent filter elements of the filter elements; and
a plurality of sensors, positions of the sensors corresponding to the positions of the holes,
wherein after the exciting beam enters the light guide plate, at least one portion of the exciting beam is transmitted to the sample through the portion of the surface of the light guide plate exposed by the holes, the sample is excited by the exciting beam to emit a signal beam, a first portion of the signal beam passes through at least one of the filter elements and travels to the sensor, and a second portion of the signal beam is shielded by at least one of the light shielding elements.

\* \* \* \* \*